United States Patent [19]

Parsons et al.

[11] Patent Number: 4,680,027
[45] Date of Patent: Jul. 14, 1987

[54] NEEDLELESS HYPODERMIC INJECTION DEVICE

[75] Inventors: James S. Parsons, Laguna Niguel; Jack S. Gasaway, Irvine, both of Calif.

[73] Assignee: Injet Medical Products, Inc., Lake Forest, Calif.

[21] Appl. No.: 808,458

[22] Filed: Dec. 12, 1985

[51] Int. Cl.$^4$ ............................................. A61M 5/30
[52] U.S. Cl. ..................................................... 604/68
[58] Field of Search .................... 604/68, 69, 70, 71, 604/72, 73; 141/2–5, 18–20

[56] References Cited

U.S. PATENT DOCUMENTS

| | | |
|---|---|---|
| Re. 24,419 | 1/1958 | Ziherl . |
| 569,887 | 2/1959 | Scherer . |
| 968355 | 9/1949 | Claude . |
| 1,212,753 | 11/1970 | Johansson . |
| 2,547,099 | 4/1951 | Smoot . |
| 2,605,763 | 8/1952 | Smoot . |
| 2,635,601 | 4/1953 | May . |
| 2,645,223 | 7/1953 | Lawshe . |
| 2,699,166 | 1/1955 | Dickinson . |
| 2,737,946 | 3/1956 | Hein, Jr. . |
| 2,764,977 | 10/1956 | Ferguson . |
| 2,800,903 | 7/1957 | Smoot . |
| 2,821,193 | 1/1958 | Ziherl . |
| 2,821,981 | 2/1958 | Ziherl . |
| 3,057,349 | 10/1962 | Ismach . |
| 3,115,133 | 12/1963 | Morando . |
| 3,138,157 | 6/1964 | Ziherl . |
| 3,202,151 | 8/1965 | Kath . |
| 3,292,621 | 12/1966 | Banker . |
| 3,292,622 | 12/1966 | Banker . |
| 3,461,867 | 8/1969 | Zimmet . |
| 3,688,765 | 9/1972 | Gasaway . |
| 3,695,266 | 10/1972 | Lussier . |
| 3,714,943 | 2/1973 | Yanof . |
| 3,763,359 | 10/1973 | Yanof et al. . |
| 3,788,315 | 1/1974 | Laurens . |
| 3,805,783 | 4/1974 | Ismach . |
| 3,815,594 | 6/1974 | Doherty . |
| 3,853,125 | 12/1974 | Clark . |
| 3,859,996 | 1/1975 | Mizzy . |
| 3,908,651 | 9/1975 | Fudge . |
| 3,933,155 | 1/1976 | Johnston . |
| 3,945,379 | 3/1976 | Pritz . |
| 3,945,383 | 3/1976 | Bennett . |
| 4,004,575 | 1/1977 | Sarstedt . |
| 4,031,889 | 6/1977 | Pike . |
| 4,059,107 | 11/1977 | Iriguchi . |
| 4,089,334 | 5/1978 | Schwebel et al. . |
| 4,103,684 | 8/1978 | Ismach . |
| 4,124,024 | 11/1978 | Schwebel et al. . |
| 4,128,098 | 12/1978 | Bloom et al. . |
| 4,301,795 | 11/1981 | Zimmermann . |
| 4,329,988 | 5/1982 | Sarnoff et al. . |
| 4,342,310 | 8/1982 | Lindmayer . |
| 4,400,172 | 8/1983 | Dettbarn . |
| 4,403,609 | 9/1983 | Cohen . |
| 4,403,989 | 9/1983 | Christensen et al. . |
| 4,421,508 | 12/1983 | Cohen . |
| 4,447,225 | 5/1984 | Taff . |
| 4,475,905 | 10/1984 | Himmelstrup . |
| 4,518,385 | 5/1985 | Lindmayer et al. . |
| 4,592,742 | 6/1986 | Landau . |
| 4,596,556 | 6/1986 | Morrow et al. . |
| 4,607,113 | 8/1985 | Dunlop . |

Primary Examiner—John D. Yasko
Attorney, Agent, or Firm—Knobbe, Martens, Olson & Bear

[57] ABSTRACT

An improved system for injecting liquid medication into the tissues of a person without using a needle to penetrate the skin includes a power supply mechanism having a source of compressed gas which drives a piston against the plunger of a syringe. The syringe has an aperture which is placed against the skin of a person and through which the liquid medication is ejected with sufficient force to pass through the skin and into the underlying tissues. The syringe is provided with a removable needle assembly so that the syringe can be filled with liquid medication in a conventional manner. The system is constructed so that the needle assembly must be removed in order to insert the needle assembly into the power supply mechanism and is also constructed so that the power supply mechanism cannot be triggered to release the compressed gas unless a syringe is inserted in the power supply mechanism and properly secured.

25 Claims, 18 Drawing Figures

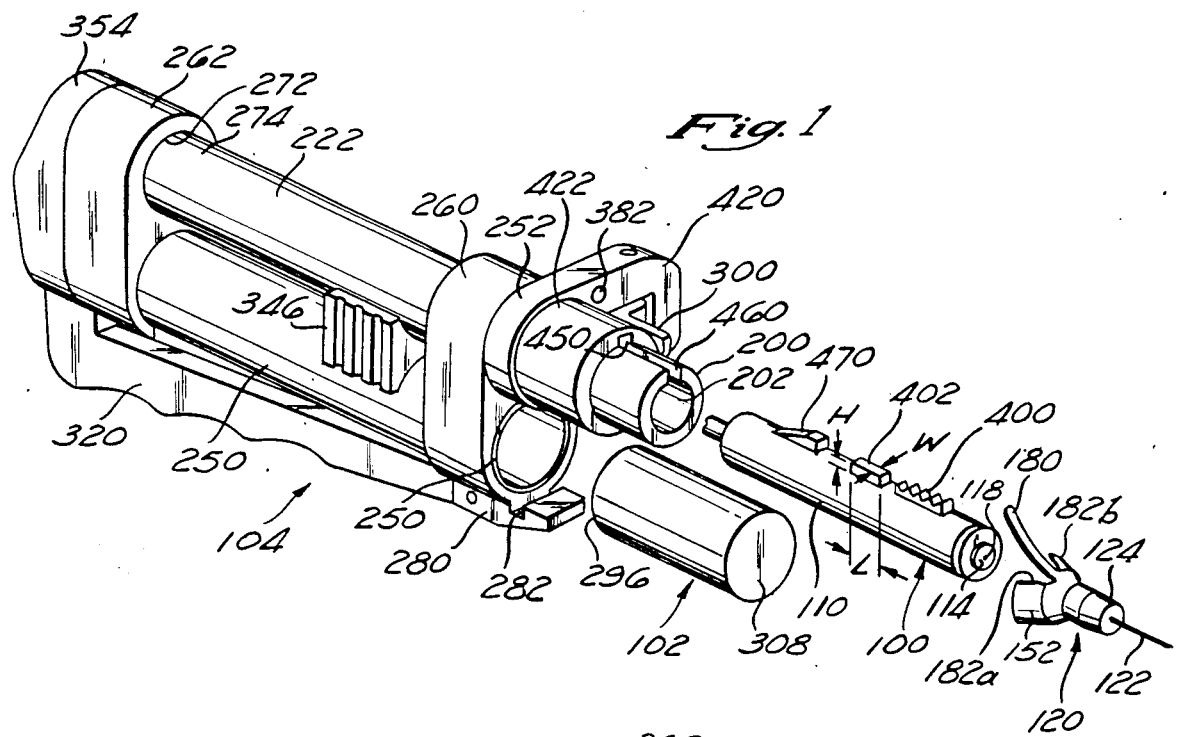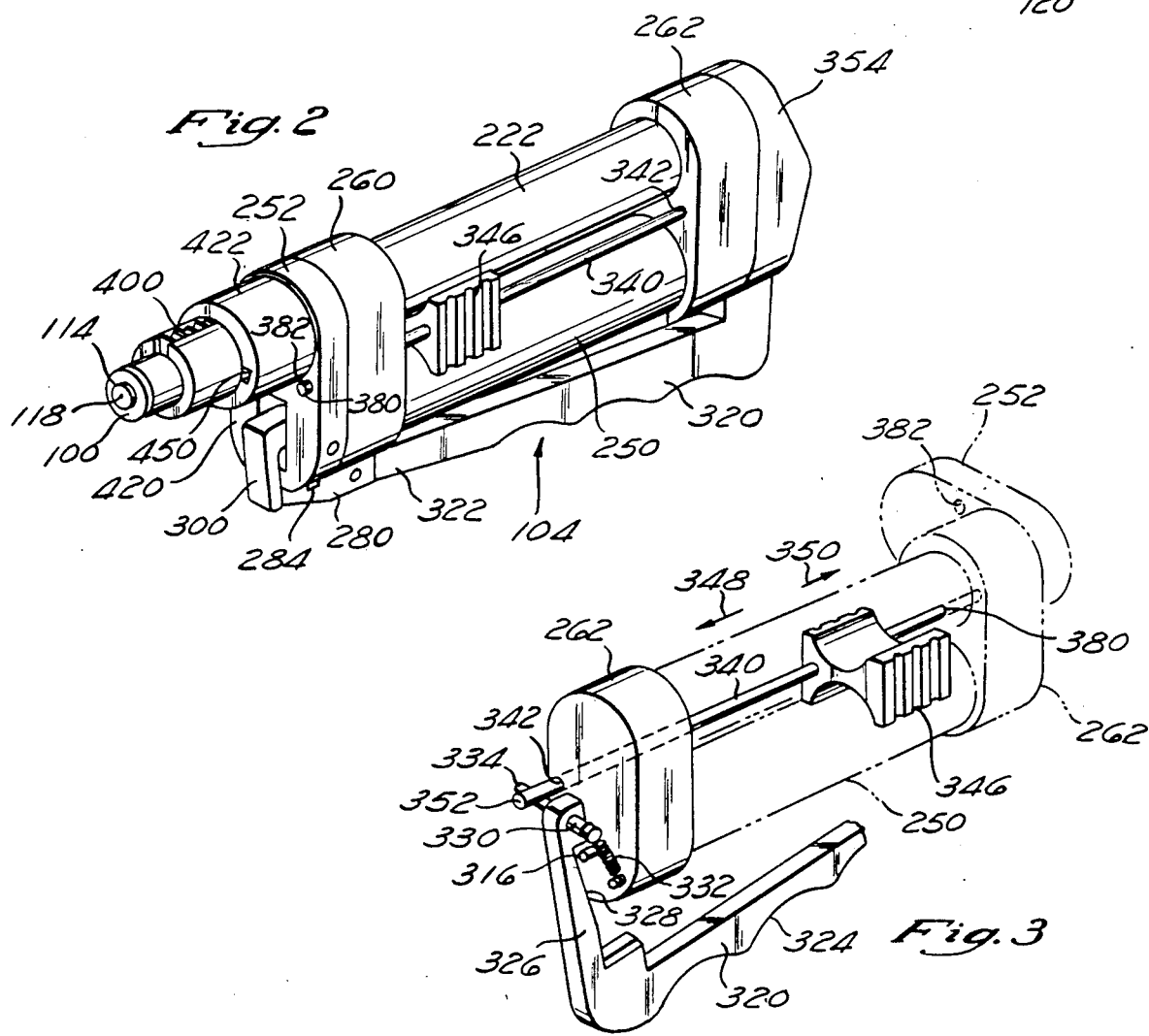

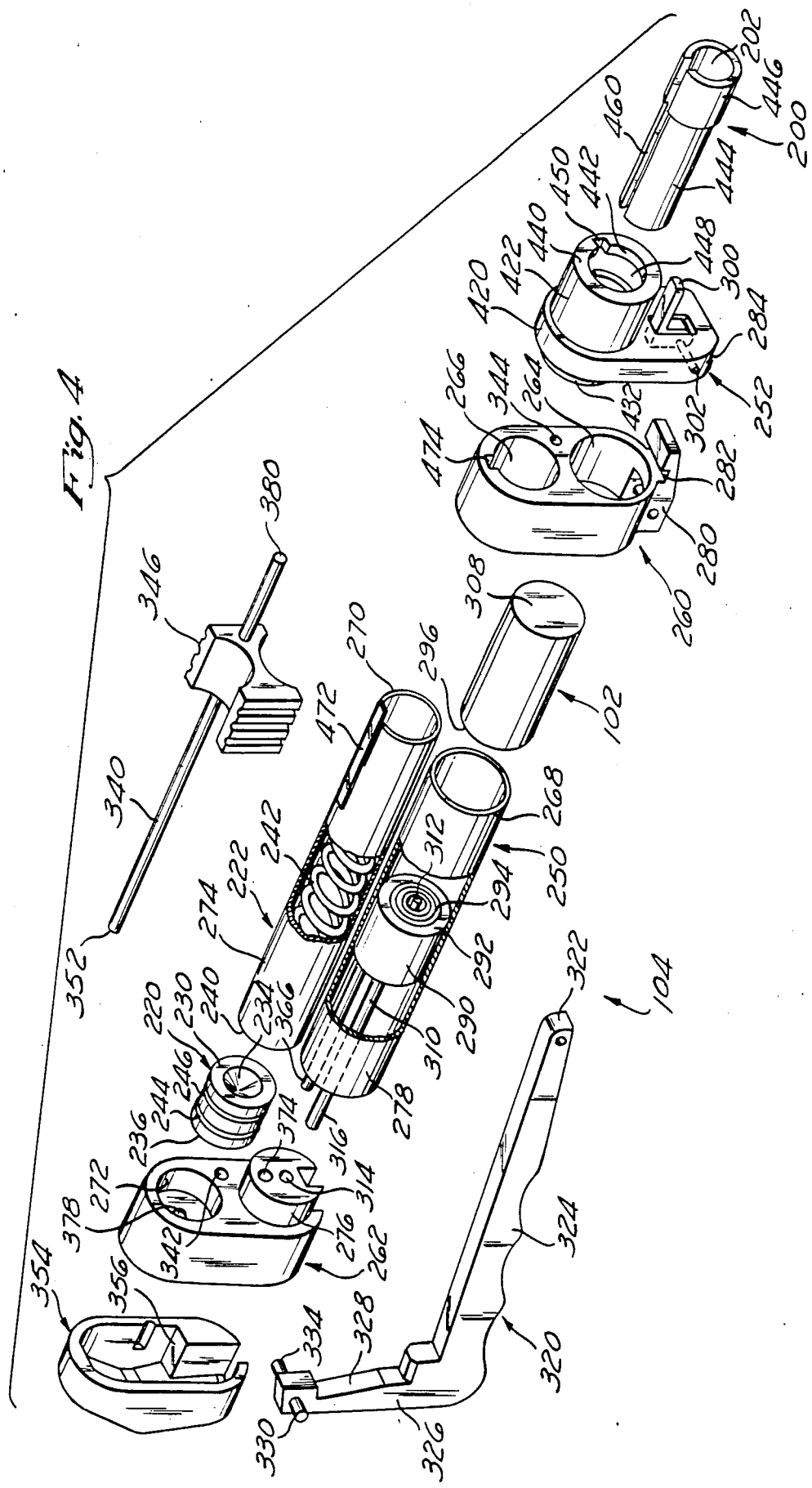

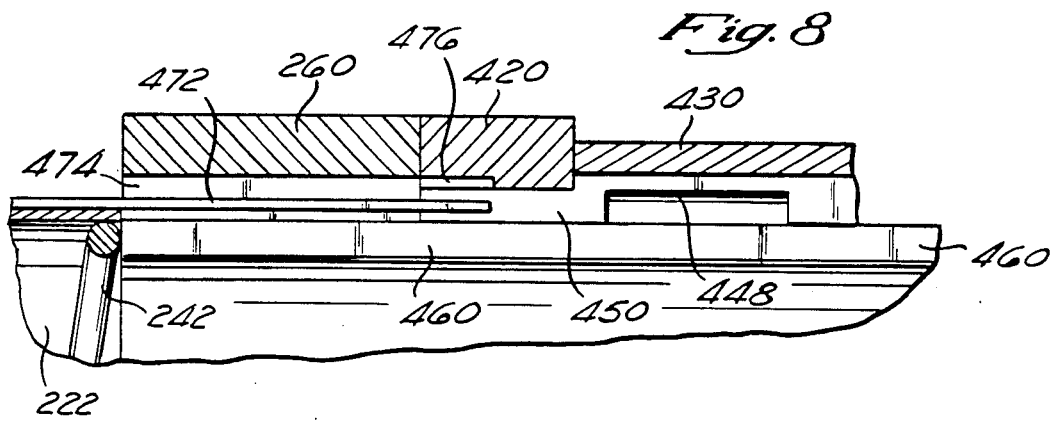
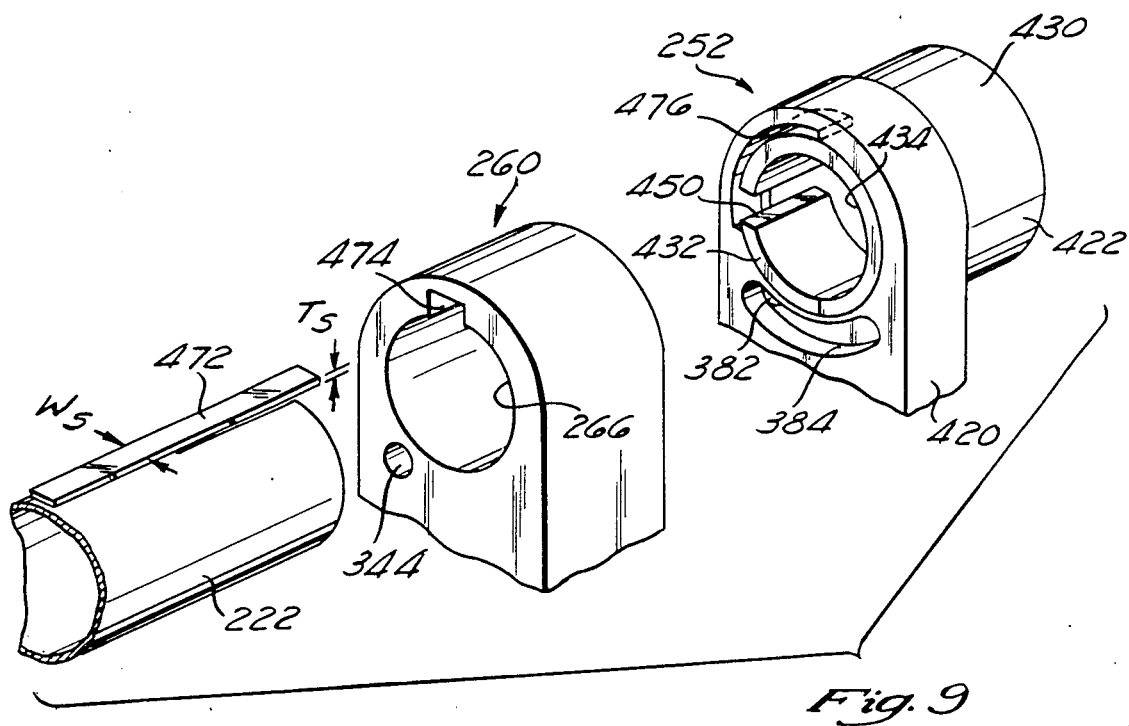
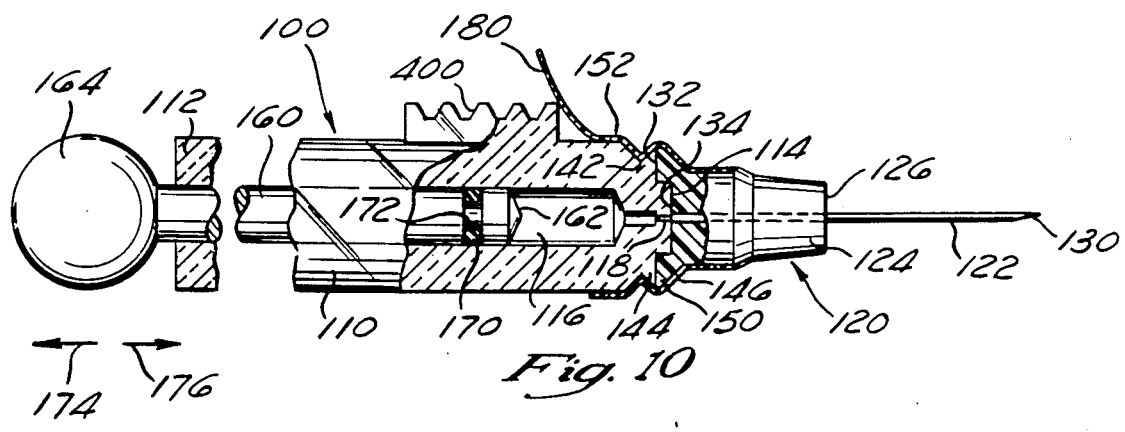

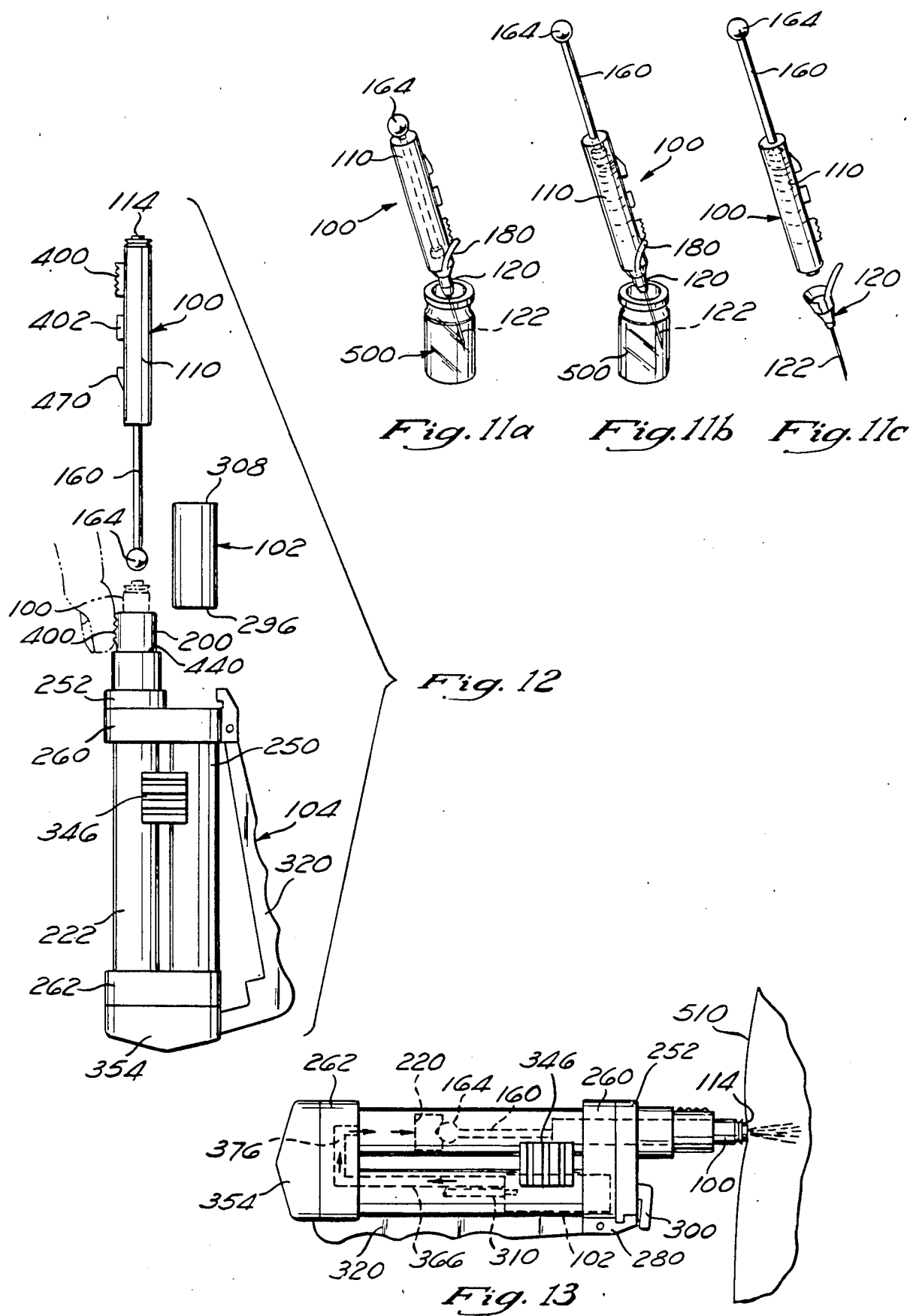

NEEDLELESS HYPODERMIC INJECTION DEVICE

FIELD OF THE INVENTION

This invention pertains to hypodermic injection devices, particularly those devices which use high pressure to inject liquid medication through the skin without piercing the skin with a needle or other instrumentality.

BACKGROUND OF THE INVENTION

There are an estimated 11 million diabetics in the United States. Of these 11 million diabetics, approximately 3 million are Type I diabetics who are insulin dependent and require an average of 1½ shots of insulin per day. The insulin must be injected in measured doses, as determined by a physician, in order to establish an appropriate concentration of insulin in a person's system. Since insulin is a protein which is broken down by gastrointestinal enzymes, it must be introduced to a person's system by injection. The most common means for injection is a syringe having an attached needle for puncturing the skin of the person so that the insulin can be injected into the tissues beneath the skin. Thus, each injection causes a puncture wound and resulting pain and discomfort. For a large number of persons, the daily (or more often) ordeal of injecting the insulin, although necessary, is practically intolerable. Thus, a need exists for an alternative means for injecting the insulin through the skin without puncturing the skin.

Numerous devices have developed in the injection art for injecting liquid medication directly through the skin of a person without requiring a needle or other apparatus for piercing or puncturing the skin. These needleless injection systems use a source of high pressure to force the liquid medication directly through the skin. Almost everyone is familiar with the high volume devices used by the military to inoculate servicemen en masse and used by various public health services to inoculate the general public as a means for preventing epidemics. The instruments used for these purposes are typically quite bulky, have a large reservoir for storage of the liquid medication, and are intended to be operated by trained personnel. The instruments are quite expensive and are unattractive for the daily use by one person for insulin injections or injections of any other self-administered medication.

Various other devices appear in the injection art which are intended to provide individualized needleless injections. Some early examples are U.S. Pat. Nos. 2,547,099 and 2,605,763 to Smoot; U.S. Pat. No. 2,645,223 to Lawshe; U.S. Pat. No. 2,635,601 to May; and U.S. Pat. No. 3,688,765 to Gasaway. The apparatuses described in the foregoing patents have limitations which appear to have reduced or prevented the widespread use of these devices by individuals. Thus, a need continues to exist for a low-cost needleless inoculation system which is safe, economical and easy to use.

SUMMARY OF THE INVENTION

The present invention is an apparatus for injecting liquid medication through the skin of a person without puncturing the skin with a needle or other penetrating device. The apparatus includes a disposable syringe which is insertable into a power supply mechanism. The disposable syringe has a hollow, tubular needle removably attached to the second end such that the needle is in substantial alignment with an aperture in one end of the syringe. The needle is insertable into a container of liquid medication so that the syringe can be filled by pulling on a plunger in a conventional manner.

The hollow, tubular needle is removable from the syringe after the liquid medication is drawn into the syringe so that the aperture in the end of the syringe can be placed in direct contact with the skin without puncturing the skin.

The power supply mechanism is constructed to receive and securely hold the syringe only after the needle is removed from the syringe. Thus, the syringe cannot be secured in the power supply mechanism with the needle attached. The power supply mechanism provides pressure to move the plunger in the syringe towards the aperture so that liquid medication in the syringe is ejected through the aperture with sufficient pressure that the liquid medication will penetrate the skin of a person when the end having the aperture is placed in substantial contact with the skin.

The power supply mechanism also includes a removable sealed container of a compressed gas, such as carbon dioxide gas. The power supply mechanism has a trigger for unsealing the sealed container to release the compressed gas into the power supply mechanism. The pressure of the compressed gas drives the plunger against the liquid medication.

The power supply mechanism also includes a safety interlocking means for preventing movement of the trigger to prevent unsealing the sealed container of compressed gas except when the syringe is secured within the power supply mechanism. The safety interlocking means includes a key on the syringe and a pivotal keyway on the end of the power supply mechanism for receiving the syringe. The keyway is pivotal from a first loading position for receiving the key on the syringe so that the syringe can be inserted into and removed from the power supply mechanism. The keyway is pivotal to a second holding position for holding the syringe so that the syringe is irremovably held in the power supply mechanism so long as the keyway is in the holding position.

The power supply mechanism further includes means for preventing the pivotal keyway from moving from the loading position to the holding position unless the syringe is fully inserted into the power supply mechanism. Thus, the trigger means cannot be activated unless the syringe is fully secured within the power supply mechanism.

The power supply mechanism and the syringe are constructed such that the syringe cannot be fully inserted into the power supply mechanism unless the needle is removed from the syringe. Since the power supply mechanism cannot be activated unless the syringe is fully inserted, and since the syringe cannot be fully inserted unless the needle is removed from the syringe, the force of the power supply mechanism cannot be applied to the liquid medication in the syringe to force the liquid medication through an attached needle. Thus, the mechanism can only be used for needleless injection.

The combination of features provided by the present invention provides significant advantages making the present invention particularly attractive for use by individuals to provide regular injections of liquid medication. The removable needle allows a user to fill the syringe from a vial of liquid medication in a conventional manner used to fill typical syringes for subcutaneous injection (i.e., injections wherein the needle penetrates the skin). Thus, a user familiar with the subcutaneous injection procedures can continue to use the same procedure for filling the syringe with liquid medication. Furthermore, the ability to fill the syringe with medication allows the user to adjust the dosage of medication to his or her individual needs unlike many of the prior devices which require the user to purchase and stock prefilled ampules having a fixed dosage. Thus, a user converting to the user of the present invention can continue to obtain his or her supply of medication from the same source rather than having to obtain special prefilled ampules intended for one injection system.

After the syringe is filled, the needle must be removed from the syringe in order to fully insert the syringe into the power supply mechanism. The power supply mechanism is constructed so that it cannot be closed unless the syringe is fully inserted and cannot be operated unless it is closed. Thus, there is no significant possibility of operating the power supply mechanism with the needle attached to the syringe. This is a particularly important safety feature since the pressures required to inject the liquid medication through the skin are too great to be safely applied to the liquid medication for subcutaneous injection with a needle.

The interlocking safety features of the power supply mechanism and the syringe also prevent the power supply mechanism from being used as an energy source for anything other than a properly inserted and secured syringe. Thus, a pencil or other similarly shaped object cannot be inserted into the power supply mechanism and ejected forcefully from the power supply mechanism as a dangerous projectile. This is a particularly important feature for home use where there is an increased possibility that the power supply mechanism can be misappropriated by juveniles or juvenile-minded persons in the user's home.

Unlike other devices known to the art, the present invention is convenient to use since the end of the syringe applied to the user's skin is presterilized when it is manufactured and, if properly handled, remains sterile until used. The syringe preferably includes a gripping mechanism to assist the user in avoiding contact with the sterile end of the syringe. The needle has to be removed to use the syringe and thus the syringe is not refillable for additional uses. Therefore, the syringe is discarded after each use. Since no other portion of the present invention contacts the injection site on the user's skin, there is no need to sterilize the power supply mechanism before or after each use. Thus, the present invention is particularly convenient for use by individual persons who may not be capable of performing or willing to perform extensive cleaning and sterilization procedures.

The present invention is particularly convenient for personal use because it has a size and shape that allows the invention to be carried in a purse or other carrying case. This is accomplished by positioning the compressed gas container in a juxtaposed, parallel relationship with the syringe rather than in a linear, coaxial relationship as shown in the prior art.

BRIEF DESCRIPTION OF THE DRAWINGS

FIG. 1 is a perspective view of the present invention showing the power supply mechanism, the compressed gas cartridge, the syringe, and the removable needle assembly, prior to insertion of the compressed gas cartridge and the syringe into the power supply mechanism.

FIG. 2 is a perspective view of the present invention from the opposite direction of the view in FIG. 1 showing the power supply mechanism with the syringe inserted and secured.

FIG. 3 is a partial perspective view of the present invention showing the safety interlock features which prevent the present invention from being triggered until the pivotal cover is closed.

FIG. 4 is an exploded view of the power supply mechanism showing the interrelationships of the internal and external parts of the mechanism.

FIG. 8 is an enlarged partial cross-sectional view taken in the area 8 in FIG. 6a showing the relationship between the end of the leaf spring and the sides of the slot in the retainer collar prior to insertion of the syringe.

FIG. 9 is a partial exploded perspective view of the cylinder with the attached leaf spring, the front barrel clamp, cartridge cover and the retainer collar showing the arcuate cavity in more detail and also showing the hole in the cartridge cover which receives the end of the safety shaft when the cartridge cover is closed.

FIG. 10 is an enlarged partial cross-sectional view of the syringe with the needle assembly attached.

FIGS. 11a, 11b, and 11c, pictorially illustrate the insertion of the needle of the syringe into a vial of liquid medication, the operation of the plunger to draw the liquid medication into the cavity of the syringe, and the removal of the needle assembly after filling the cavity, respectively.

FIG. 12 pictorially illustrates the insertion of the compressed gas cartridge and the syringe into the power supply mechanism and shows the use of the gripping projection to avoid touching the sterile end of the syringe.

FIG. 13 pictorially illustrates the activation of the trigger handle of the power supply mechanism to release the compressed gas and push the piston against the plunger of the syringe, thereby ejecting the liquid medication from the syringe and through the skin of a person.

DETAILED DESCRIPTION OF THE PREFERRED EMBODIMENT

Figure 5:
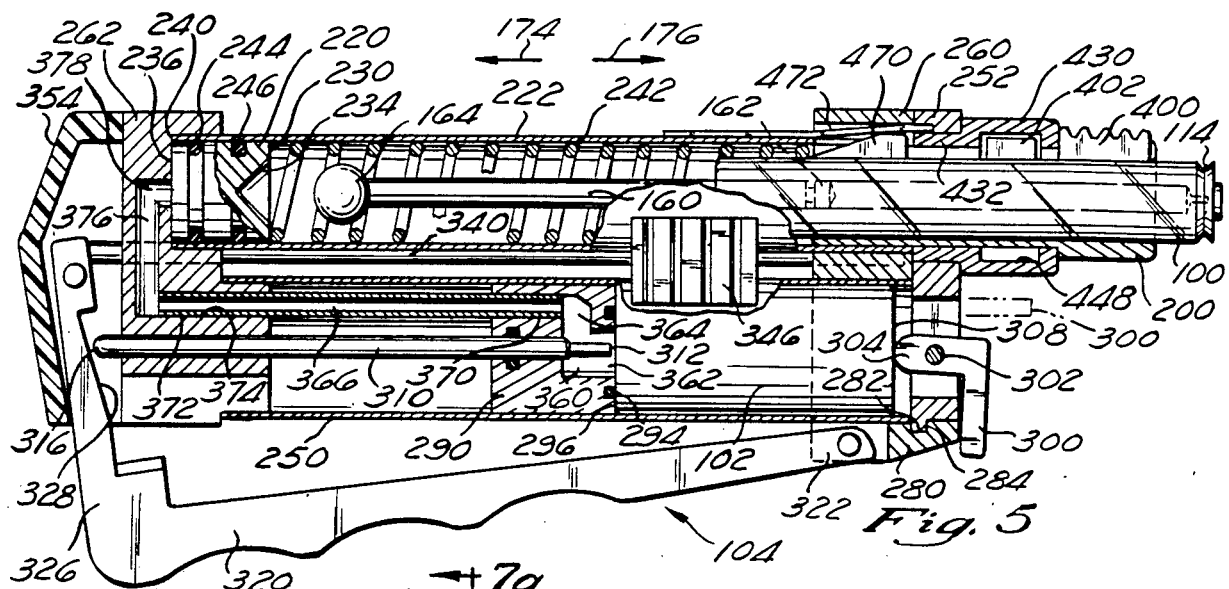
FIG. 5 is a cross-sectional view of the power supply mechanism with the syringe and the compressed gas cartridge installed.

A preferred embodiment of the apparatus of the present invention for injecting liquid medication through the skin of a person without piercing the skin is shown in FIG. 1. The apparatus comprises a disposable syringe 100, a disposable compressed gas cartridge 102, and a power supply mechanism 104. The disposable syringe 100 and the disposable compressed gas cartridge 102 are insertable into the power supply mechanism 104 and operate in conjunction with the power supply mechanism 104 to eject a liquid medication from the syringe 100.

The syringe 100, shown in more detail in FIG. 10, comprises a tubular central body portion 110 having an open first end 112 and a substantially closed second end 114 to form an enclosed cavity 116 within the central body portion 110. The second end 114 has an aperture 118 formed therein to provide a means for fluid communication through the second end 114 into the cavity 116. A needle assembly 120 is removably attached to the second end 114 of the central body portion 110 in substantial alignment with the aperture 118. The needle assembly 120 is shown in FIG. 10 attached to the central body portion 110 and is shown in FIG. 1 after being detached from the central body portion 110. The needle assembly 120 includes a hollow tubular needle 122 that is similar to conventional hypodermic needles used for the injection of insulin and other liquid medications. The needle 122 has a longitudinally disposed central bore which extends axially through the needle 122 so that liquid medication can flow through the needle 122. The needle 122 is supported by a needle base 124 and extends through the needle base 124. A portion of the needle 122 extends from a first end 126 of the needle base 124 and has a first end 130 which is cut at an oblique angle to the longitudinal axis to form a sharp point. The needle base 124 has a second end 132 which is constructed to have a snug fit with the second end 114 of the central body portion 110. The needle 122 has a second end 134 which extends substantially to the second end 132 of the needle base 124. When the second end 132 of the needle base 124 is positioned on the second end 114 of the central body portion 110, the second end 134 of the needle 122 is aligned with the aperture 118.

The central body portion 110 advantageously includes an annular groove 142 which forms a depressed ring around the central body portion at a location proximate to the second end 114. The annular groove 142 is displaced a sufficient distance from the second end 114 so that a shoulder portion 144 is formed between the annular groove 142 and the second end 114. The needle base 124 has a tapered portion 146 proximate to the second end 132 of the neeedle base 124 so that the second end 132 has a diameter approximately the same as the diameter of the second end 114 of the central body portion 110 and so that the diameter of the needle base 124 becomes smaller along the tapered portion 146 as the distance from the second end 132 of the needle base 124 becomes greater. Thus, the needle base 124 has an annular shoulder portion 150 between the second end 132 of the needle base 124 and the tapered portion 146. The needle base 124 is secured to the second end 114 of the central body portion 110 by a collar 152. In the preferred embodiment, the collar 152 is a section of heat shrinkable tubing 152 which has an inside diameter before shrinking that is slightly larger than the outside diameters of the needle base 124 and the central body portion 110. When heat is applied to the heat shrinkable tubing 152, the tubing 152 shrinks radially so that the inside diameter of the tubing 152 becomes smaller and the tubing 152 becomes tightly bound to both the needle base 124 and the central body portion 110. At the same time, the tubing 152 shrinks longitudinally so that the length of the tubing 152 along the central body portion 110 and the needle base 124 tries to become shorter. The tubing 152 is bound to the shoulder 144 of the central body portion 110 and is bound to the shoulder 150 of the needle base 124. Thus, as the tubing 152 shrinks longitudinally the shoulder 144 of the central body portion 110 and the shoulder 150 of the needle base 124 are drawn together longitudinally to mate the second end 114 of the central body portion 110 tightly together with the second end 132 of the needle base 124. Thus, the heat shrinkable tubing 152 causes an air-tight and liquid-tight seal to be formed between the central body portion 110 and the needle base 124 so that the needle 122 is effectively an extension of the fluid communication path into the cavity 116 formed by the aperture 118. When the needle assembly 120 is attached to the central body portion 110, the needle 122 is insertable into a container of a liquid medication in a conventional manner used to fill hypodermic syringes (i.e., the needle 122 advantageously pierces a seal of a vial of liquid medication so that the needle is in fluid contact with the liquid medication therein).

The syringe 100 further includes a plunger 160, shown more clearly in FIG. 10 and in the partial cross-sectional view in FIG. 5. The plunger 160 has a first end 162 within the cavity 116 of the central body portion 110 and has a second end 164 extending out of the cavity 116 in a direction opposite the second end 114 of the central body portion 110. The second end 164 is preferably enlarged to provide a head 164 that can be gripped by a person using the syringe 100 and to which force can be applied to move the plunger 160. In the preferred embodiment, the second end or head 164 of the plunger 160 is ball-shaped. At a location proximate to the first end 162, the plunger 160 preferably includes an O-ring 170 positioned in an annular groove 172. The O-ring 170 preferably has an outside diameter which is slightly larger than the inside diameter of the cavity 116 so that the O-ring 170 is compressed when the plunger 160 is in the cavity 116. Thus, the O-ring 170 forms an air-tight seal in the cavity 116. The plunger 160 is moveable within the cavity 116 by gripping the head 164 and pulling the plunger 160 in a first direction 174 away from the second end 114, as indicated by an arrow 174, to create a vacuum within the cavity 116 to draw a liquid medication through the needle 122 and the aperture 118 into the cavity 116. The plunger 160 is moveable in a second direction 176 towards the second end 114 of the central body portion 110, as indicated by an arrow 176, by pushing on the head 164 of the plunger 160 to force the liquid medication from the cavity 116 through the aperture 118 in the second end 114.

The needle assembly 120 is removable from the second end 114 of the central body portion 110 after drawing the liquid medication into the cavity 116 of the central body portion 110 so that the second end 114 of the central body portion 110 can be placed in contact with the skin of a person without penetrating the skin.

The needle assembly 120 is shown in the removed condition in FIG. 1. In the preferred embodiment, the heat shrinkable tubing 152 which forms the collar 152 holding the needle assembly 120 to the second end 114 of the central body portion 110 has a tab 180 which provides a means for gripping the heat shrinkable tubing. The heat shrinkable tubing 152 is weakened along lines 182a and 182b (FIG. 1) which are aligned with the tab 180. The tubing 152 may be weakened along the lines 182a and 182b by perforations or other known means conventionally used to provide sealed bottle caps and other product containers in the pharmaceutical field and in other consumer product fields. When force is applied to the tab 180 in a direction to apply force to the weakened portions along the lines 182a and 182b, the tubing 152 parts to allow the needle assembly 120 to be disengaged from the second end 114 of the central body portion 110.

The power supply mechanism 104 is constructed to receive and securely hold the syringe 100 only after the needle assembly 120 is removed from the second end 114 of the central body portion 110. As will be set forth in more detail below, the power supply mechanism 104 has a front muzzle piece 200 which has a bore 202 for receiving the syringe 100. The bore 202 has a diameter that is slightly larger than the outside diameter of the central body portion 110 of the syringe 100. For example, in the preferred embodiment, the diameter of the bore 202 is approximately 0.015 inch larger than the outside diameter of the central body portion 110. Preferably, the thickness of the heat shrinkable tubing 152 which forms the collar 152 to hold the needle assembly 120 to the central body portion 110 is selected so that the outside diameter of the collar 152 in place on the central body portion 110 is greater than the diameter of the bore 202 of the muzzle piece 200. Furthermore, the tab 180 is preferably disposed at an angle to the central body portion 110 and cannot be inserted into the bore 202. Thus, the syringe 100 cannot be fully inserted into the power supply mechanism 104 with the needle assembly 120 held in place by the collar 152.

The power supply mechanism 104 is constructed to provide pressure against the head 164 of the plunger 160 to move the plunger 160 in the second direction 176 towards the second end 114 of the central body portion 110 of the syringe 100 so that the liquid medication in the cavity 116 of the syringe 100 is ejected through the aperture 118 of the second end 114 of the central body portion 110 with sufficient pressure so that the liquid medication will penetrate the skin of a person when the second end 114 is placed in substantial contact with the skin.

Referring now to FIGS. 4 and 5, the power supply mechanism 104 comprises a resiliently biased moveable piston 220 within a cylinder 222. The cylinder 222 is aligned with the muzzle piece 200 and thus with the bore 202. The piston 220 thus has an axis of movement within the cylinder 222 substantially aligned with the first direction 174 and second direction 176 of movement of the plunger 160 within the central body portion 110 of the syringe 100 when the syringe 100 is positioned in the bore 202. The piston 220 has a first facing surface 230 directed towards the syringe 100 when the syringe 100 is in the power supply mechanism 104. The first facing surface 230 has an indented portion 234 substantially centered on the facing surface 230. The indented portion 234 is aligned with the second end or head 164 of the plunger 160 so that the head 164 is held in the center of the facing surface 230 when the facing surface 230 is pressed against the head 164 of the plunger 160. In one preferred embodiment, the indented portion 234 has a conical shape as shown in FIG. 5. The piston 220 has a second facing surface 236 directed away from the syringe 100. The piston 220 is biased to a position in the cylinder 222 towards an end 240 of the cylinder 222 away from the syringe 100 in the power supply mechanism 104. The biasing is accomplished in the preferred embodiment by a coil spring 242 held within the cylinder 222. The piston 220 preferably has one or more O-rings such as O-rings 244 and 246 which form annular rings around the piston 220 so that piston 220 has a gas tight fit with the inner surface of the cylinder 222.

The power for operating the power supply mechanism 104 is provided by the disposable gas cartridge 102 which is a sealed container of a compressed gas. Preferably, the compressed gas is carbon dioxide at a pressure of approximately 800 pounds per square inch. At this pressure and at a temperature of approximately 70 degrees, the carbon dioxide is actually a liquid within the gas cartridge 102. The carbon dioxide vaporizes as soon as it is released from the pressure in the gas cartridge 102.

The sealed container or gas cartridge 102 is inserted into a lower barrel 250 of the power supply mechanism 104 and held in place by a pivotal cover 252. The pivotal cover 252 is shown in an open position in FIG. 1 so that the gas cartridge 102 can be inserted into the lower barrel 250. In FIG. 2, the pivotal cover 252 is shown in a closed position so that the gas cartridge 102 (not shown) is held securely within the lower barrel 250.

In the preferred embodiment shown herein, the lower barrel 250 and the cylinder 222 are held in a fixed relationship by a front end barrel clamp 260 and a rear breechblock 262. As shown more clearly in FIG. 4, the front end barrel clamp 260 has a lower circular opening 264 and an upper circular opening 266 for receiving the outside of a front portion 268 of the lower barrel 250 and the outside of a front portion 270 of the cylinder 222, respectively, so that the barrel 250 and the cylinder 222 are held in a fixed over-under relationship. The rear breechblock 262 has an upper circular opening 272 for receiving the outside of a rear portion 274 of the cylinder 222 and thus receives the end 240 of the cylinder 222. The rear breechblock 262 has a substantially circular lower pedestal 276 which is positioned to receive the inner surface of a rear portion 278 of the lower barrel 250. The front end barrel clamp 260 and the rear breechblock 262 are each secured to the cylinder 222 and the lower barrel 250 by screws, welding, or other fastening means. The front end barrel clamp 260 has an extended lower portion 280 which has a slot 282 therein for receiving a protrusion or lip 284 on the pivotal cover 252. The protrusion 284 is shown more clearly in cross-section in FIG. 5. The mechanical interaction of the protrusion 284 with the slot 282 prevents movement of the pivotal cover 252 in a forward direction after the pivotal cover 252 is pivoted on the position shown in FIGS. 2 and 5.

The lower barrel 250 includes a cylindrical firing pin block 290 which has an outside diameter substantially equal to inside diameter of the lower barrel 250. The firing pin block 290 has a mating surface 292 which has an O-ring 294 positioned substantially concentric with the center of the mating surface 292. The firing pin block 290 is positioned in the lower barrel 250 at distance from the front of the lower barrel 250 which is slightly greater than the length of the gas cartridge 102 to be inserted into the barrel. When the gas cartridge 102 is inserted into the barrel, a first end 296 of the cartridge 102 is positioned proximate to the mating surface 292 against the O-ring 294. The pivotal cover 252 is pivoted to a position over the lower barrel 250 to enclose the gas cartridge 102 within the lower barrel 250. The pivotal cover 252 has a camming lever 300 which is pivotally mounted to the pivotal cover by a pin 302 or other means. When the camming surface 300 is in an open position, as shown in FIGS. 1 and 4, the pivotal cover 252 can be opened and closed. When the pivotal cover 252 is closed as shown in FIGS. 2 and 5, the camming lever 300 is operable to a closed position to force an eccentric portion 304 of the camming lever 300 against a second end 308 of the gas cartridge 102 opposite said first end 296 of the gas cartridge 102. The operation of the eccentric portion 304 of the camming lever 300 against the second end 308 of the gas cartridge 102 forces the first end 296 of the gas cartridge 102 against the O-ring 294 to form gas tight seal between the gas cartridge 102 and the mating surface 292 of the firing pin block 290.

The firing pin block 290 conducts a means for unsealing the sealed container or gas cartridge 102 to release the compressed gas after the cartridge is inserted in the lower barrel 250. The means for unsealing is a firing pin 310 which passes through the approximate center of the firing pin block 290. The firing pin 310 is a rod which has a first end 312 which has an outer diameter sufficiently small that it can enter the first end 296 of the gas cartridge 102 and release the compressed gas stored therein. Preferably, the first end 296 of the gas cartridge 102 has a seal portion (not shown) which is penetrable by the first end 312 of the firing pin 310. For example, the gas cartridge 102 can advantageously be a conventional metallic cartridge which has a portion on the first end 296 which comprises thinner material which is more easily penetrable by the first end 312 of the firing pin 310. The firing pin 310 passes through a hole 314 in the rear breechblock 262 and has a second end 316 which extends beyond the breechblock 262 and is positioned for mechanical interaction with a moveable trigger means 320 so that sealed gas cartridge 102 is unsealed when force is applied to the trigger means 320. The trigger means 320 in the preferred embodiment is an L-shaped handle 320 which has a first end 322 pivotally attached to the lower portion 280 of the front barrel clamp 260, a gripping portion 324 forming the shaft of the L-shape, and a camming portion 326 forming the base of the L-shape. The camming portion 326 has a camming surface 328 positioned proximate to the second end 316 of the firing pin 310. When the trigger handle 320 is operated by applying force to position the gripping portion 324 closer to the lower barrel 250, the camming surface 328 pushes against the second end 316 of the firing pin 310 to force the firing pin 310 towards the gas cartridge 102. When this occurs, the first end 312 of the firing pin 310 penetrates the seal of the gas cartridge 102 and releases the compressed gas (or fluid) contained therein.

As shown in FIG. 3, the camming portion 326 preferably includes a first ear 330. A spring 332 has a first end attached to the first ear 330 of the camming portion 326 and a second end attached to the rear breechblock 262. The spring 332 pulls against the first ear 330 to bias the gripping portion 324 of the handle 320 away from the lower barrel 250 and thus biases the handle 320 to the non-triggered position shown in FIG. 3. The camming portion 326 also preferably includes a second ear 334, which may advantageously be an extension of a pin forming the first ear 330 as shown in FIG. 3. The second ear 334 is positioned to mechanically interact with a safety shaft 340 which is slidable between the rear breechblock 262 and the front barrel clamp 260 (see FIG. 4). The safety shaft 340 slides through a hole 342 in the rear breechblock 262 and a hole 344 in the front barrel clamp 260. The safety shaft 340 has a finger grip 346 mounted to it intermediate the rear breechblock 262 and the front barrel camp 260. The finger grip 346 provides a means for moving the safety shaft 340 in a direction 348 and a direction 350, indicated by an arrow 348 and an arrow 350, respectively. As shown in FIG. 3, the finger grip 346 is preferably symmetrical with respect to the sides of the lower barrel 250 and the cylinder 222 so that the finger grip 346 can be operated equally well by a left-handed and a right-handed person. When the safety shaft 340 is moved toward the rear breechblock 262 in the direction 348, a first end 352 of the safety shaft 340 extends through and beyond the rear breechblock 262 into the path of movement of the second ear 334 of the camming portion 326 of the trigger handle 320. When the safety shaft 340 is in this rearmost position, the trigger handle 320 cannot be forced towards the lower barrel 250 by an amount sufficient to force the first end 312 of the firing pin 310 through the seal of the gas cartridge 102, thus blocking the triggering of the power supply mechanism 104. When the safety shaft 340 is moved in the direction 350 towards the front barrel clamp 260, the first end 352 of the safety shaft 340 is moved out of the path of the second ear 334 so that the camming surface 328 of the camming portion 326 can be moved against the second end 316 of the firing pin 310. Thus, when the safety shaft 340 is moved forward, the power supply mechanism 104 is unblocked and can be triggered by applying force to the gripping portion 324 of the trigger handle 320. As will be explained more fully below, the safety shaft 340 also interacts with the pivotal cover 252 so that the safety shaft 340 cannot be moved towards the front barrel clamp 260 unless the pivotal cover 252 is closed.

Returning briefly to FIGS. 1 and 2, the power supply mechanism 104 further includes a rear cover 354 which is placed over the rear of the power supply mechanism 104 to protect the safety interlock features described above in connection with FIG. 3. As shown in FIG. 4, the rear cover 354 advantageously includes a projected ledge 356 which provides a lower stop for the second ear 334 of the camming portion 326 of the trigger handle 320 to thereby limit the movement of the trigger handle 320 away from the lower barrel 250 of the power supply mechanism 104.

The power supply mechanism 104 includes means for conducting the compressed gas released from the gas cartridge 102 to the second facing surface 236 of the piston 220. The compressed gas from the cartridge 102 is released into a cavity 360 (FIG. 5) in the firing pin block 290. The cavity 360 has an inlet portion 362 formed in the mating surface 292 of the firing pin block 290 within a circle formed by the O-ring 294. Thus, the compressed gas released from the gas cartridge 102 is constrained by the O-ring 294 to enter the cavity 360 through the inlet portion 362. The cavity 360 has an outlet portion 364 which provides a path for releasing the compressed gas from the cavity 360. A tube 366 has a first end 370 which is connected to the outlet portion 364 by press fitting or other means. The tube 366 has a second end 372 which is connected to a hole 374 in the rear breechblock 262. This connection can also advantageously be accomplished by press fitting or other means. The hole 374 in the breechblock 262 is an inlet end 374 of a U-shaped gas conducting path 376 through the breechblock 262. The gas conducting path 376 turns within the breechblock 262 and has an outlet end 378 which is proximate to the second facing surface 236 of the piston 220 in the cylinder 222. Thus, the compressed gas released from the gas cartridge 102 is conducted to the second facing surface 236 of the piston 220 to apply a force on the second surface 236 of the piston 220 so that the piston 220 is moved in the second direction 176 against the resilient biasing of the spring 242. The indented portion 234 of the first facing surface 230 of the piston 220 engages the head 164 of the plunger 160 and forces the plunger 160 to move in the second direction 176 causing the first end 162 of the plunger 160 to eject the liquid medication in the cavity 116 through the aperture 118 in the second end 114 of the central body portion 110 with a pressure sufficient to force the liquid medication through the skin. In the preferred embodiment, the second facing surface 236 of the piston 220 has a diameter of approximately 0.495 inch and thus has a surface area of approximately 0.192 square inch. Thus, when the compressed gas is released from the gas cartridge 102 at a pressure of approximately 800 pounds per square inch, a force of approximately 154 pounds is applied to the piston 220. Only a small amount of spring force is required to bias the piston 220 towards the breechblock 262 when the power supply mechanism 104 is not triggered. Thus, very little of the force applied to the piston 220 is required to overcome the resilient biasing of the spring 242 and approximately 150 pounds of force is applied to the second end 164 of the plunger 160. The outside diameter of the plunger 160 and the inside diameter of the cavity 116 in the central body portion 110 are approximately equal to 0.138 inch. Thus, the surface area of the liquid medication against which the first end 162 of the plunger 160 is forced is approximately 0.015 inch, or approximately one-twelfth of the surface area of the second facing surface 236 of the piston 220. The pressure applied to the liquid medication is theoretically in excess of 10,000 pounds per square inch; however, frictional losses between the O-rings 244 and 246 of the piston 220 and the inner surface of the cylinder 222, frictional losses between the O-ring 170 of the plunger 160 and the inner surface of cavity 116, and frictional losses caused by the movement of the compressed gas and the movement of the liquid medication reduces the actual pressure of the fluid ejected through the aperture 118 to a magnitude on the order of 4,000 to 5,000 pounds per square inch. This pressure is more than sufficient to force the liquid medication through the skin and into the muscles and other tissues beneath the skin. The spring constant of the spring 242 can be increased to further reduce the pressure applied to the liquid medication. Alternatively, a needle valve (not shown) can be provided to reduce the flow of the gas in the gas conducting path 376 to thereby reduce the pressure applied to the liquid medication in the syringe 100.

As set forth above, the apparatus of the present invention includes a safety interlocking means in the form of the safety shaft 340 for preventing movement of the trigger handle 320 and thus of the firing pin 310 to thereby prevent the firing pin 310 from unsealing the sealed container 102 of compressed gas except when the syringe 100 is secured within the power supply mechanism 104. The safety shaft 340 has a second end 380 which extends through the hole 344 in the front barrel clamp 260 and is selectively engageable with a hole 382 in the pivotal cover 252. (See FIG. 9) In order to engage the second end 380 of the safety shaft 340 in the hole 382 of the pivotal cover 252, the pivotal cover 252 must be fully closed over the lower opening 264 in the front barrel clamp 260 so that the hole 382 is aligned with the second end 380 of the safety shaft 340. Thus, the gas cartridge 102 is fully secured within the lower barrel 250 by the interaction of the slot 282 of the extended portion 280 of the front barrel clamp 260 with the lip 284 of the pivotal cover 252. Thus, the pressure of the compressed gas released from the cartridge 102 cannot force the cartridge 102 from the lower barrel 250 so that the cartridge 102 becomes a dangerous projectile. If the pivotal cover 252 is not fully closed, the hole 382 in the pivotal cover 252 will not be aligned with the second end 380 of the safety shaft 340 and the safety shaft 340 cannot be moved forward in the direction 350 (FIG. 3) to unblock the second ear 334 of the camming portion 326 of the trigger handle 320. As will be described in detail below, the action of closing the pivotal cover 252 also locks the syringe 100 into the power supply mechanism 104 so that the syringe 100 cannot be ejected from or otherwise removed from the power supply mechanism 104 when the pivotal cover 252 is fully closed.

As shown in FIG. 9, the pivotal cover 252 also preferably includes an arcuate slot 384 which has one end aligned with the hole 382. The arcuate slot 382 acts as a guide for the second end 380 of the safety shaft 340 (not shown) when the safety shaft 340 is not engaged in the hole 382. Furthermore, the interaction of the ends of the arcuate slot 382 with the second end 380 of the safety shaft 340 limits the movement of the pivotal cover 252 from its fully open to its fully closed position. As shown in FIGS. 1 and 5, the syringe 100 has three projections disposed along the outside surface of the central body portion 110. A first gripping projection 400 preferably has a series of ridges which provide a means for securely gripping the central body portion 110 for inserting and removing the syringe 100 into and from the power supply mechanism 104. The gripping projection 400 is disposed away from the second end 114 of the central body portion 110 by a distance sufficient to substantially reduce the probability that a person holding the syringe 100 by the gripping projection 400 will touch the second end 114 and contaminate the aperture 118 through which the liquid medication will be ejected into the person's skin.

A second projection 402 is a keying tab 402 which, as will be described fully below, interacts with the pivotal cover 252 to prevent the syringe 100 from being removed from the power supply mechanism 104 after the pivotal cover 252 has been fully closed. The keying tab 402 has a length L extending in a direction between the first end 112 and the second end 114 of the central body portion 110, has a width W in a direction tangential to the outer circumference of central body portion 110, and has a height H in a radial direction with respect to the central body portion 110.

As shown in FIGS. 1–9, the pivotal cover 252 comprises a cartridge cover 420 and a retainer collar 422 which pivot together to hold the compressed gas cartridge 102 and the syringe 100 in place in the power supply mechanism 104. The operation of the cartridge cover 420 to hold the compressed gas cartridge 102 has been described above with respect to the pivotal cover 252. The retainer collar 422 has a front large portion 430 having a first outer diameter and a rear small portion 432 having a second outer diameter smaller than the first outer diameter. (See the cross sectional views in FIGS. 5, 6a and 6b.) The rear small portion 432 of the retainer collar 422 is press fit into and secured within a bore 434 in the cartridge cover 420. Thus, the retainer collar 422 and the cartridge cover 420 pivot together as one unit.

The front portion 430 of the retainer collar 422 has a front surface 440. The front surface 440 has a central bore therein to form an inner surface 442 having a diameter slightly larger than the outer diameter of a rear portion 444 of the muzzle piece 200 and slightly smaller than the outer diameter of a front portion 446 of the muzzle piece 200. The outer diameter of the rear portion 444 of the muzzle piece 200 is selected to be substantially equal to the inside diameter of the front portion 270 of the cylinder 222. In one embodiment of the present invention, the rear portion 444 of the muzzle piece 200 is press fit into the front portion 270 of the cylinder 222. Additional means, such as set screws or the like, can be used to fasten the rear portion 444 of the muzzle piece 200 within the front portion 270 of the cylinder 222. The muzzle piece 200 provides a bearing surface for the pivotal cover 252 so that the cartridge cover 420 and the retainer collar 422 can be pivoted with respect to the front barrel clamp 260. The cartridge cover 420 and the retainer collar 422 pivot about the rear portion 444 of the muzzle piece 200. The larger outer diameter of the front portion 446 of the muzzle piece 200 constrains the retainer collar 422 from forward movement by the action of the front portion 446 of the muzzle piece 200 on the front surface 440 of the retainer collar 422.

Figure 6A:
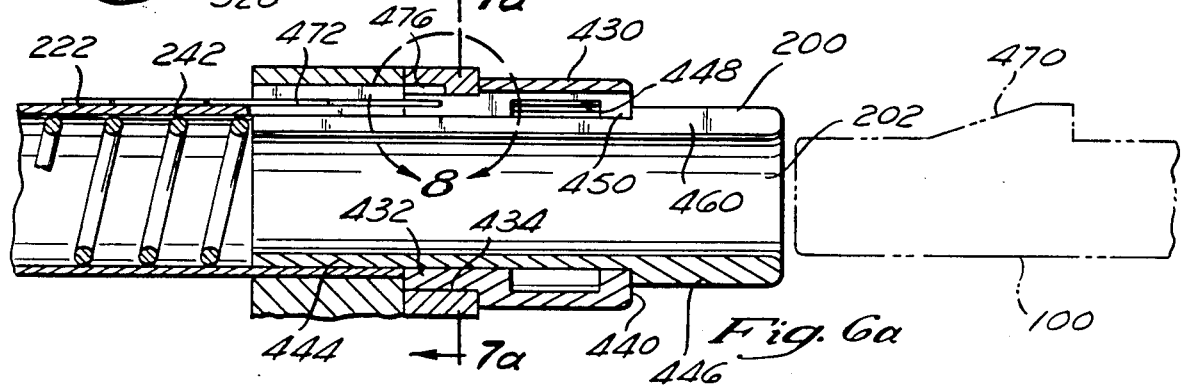
FIG. 6a is a partial cross-sectional view of the front barrel clamp, the retainer collar and the muzzle piece prior to insertion of the syringe and closure of the pivotal cover to show the interaction of the leaf spring with the retainer collar to prevent closure of the pivotal cover.
Figure 6B:
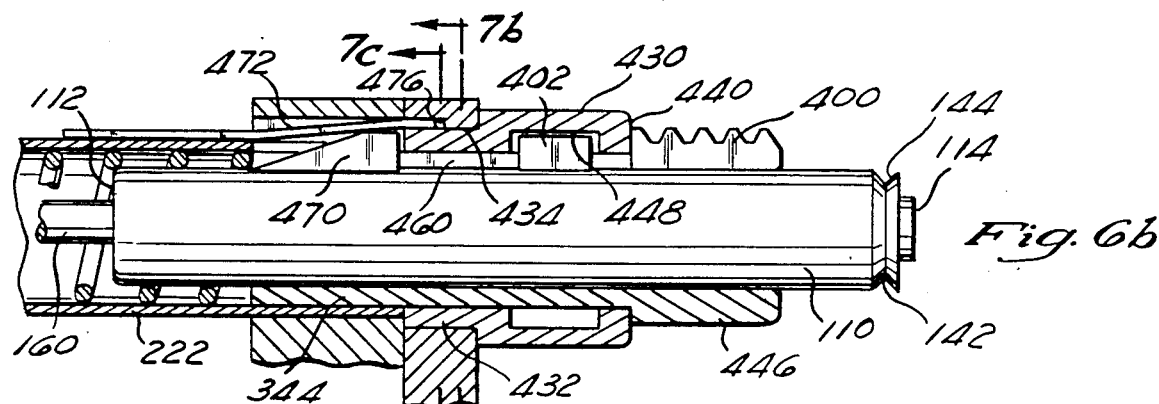
FIG. 6b is a partial cross-sectional view of the front barrel clamp, the retainer collar and the muzzle piece after insertion of the syringe and closure of pivotal cover showing the leaf spring pushed into the arcuate cavity to allow the retainer collar to be pivoted.

An annular raceway 448 is formed in the inner surface 442 of the retainer collar 422 as shown in FIG. 4 and in cross-section in FIGS. 5, 6a and 6b. The annular raceway 448 is formed in the inner surface 442 with a depth perpendicular to the inner surface 442 slightly larger than the height H of the keying tab 402 of the syringe 100 and a width slightly greater than the length L of the keying tab 402 of the syringe 100. A slot 450 extends from the front surface 440 through the front portion 430 and the rear portion 432 of the retainer collar 422. The slot 450 has a width slightly larger than the width W of keying tab 402 on the central body portion 110 of the syringe 100 and has a height slightly larger than the height H of the keying tab 402. Thus, the keying tab 402 can be inserted into the slot 450. As shown in FIGS. 5 and 6b, the keying tab 402 is spaced apart from the gripping projection 400 by a distance selected so that the gripping projection 400 will strike the front surface 440 of the retainer collar 422 when the keying tab 402 is aligned with the annular raceway 448 of the retainer collar 422. The height of the gripping projection 400 is advantageously selected so that the gripping projection 400 cannot enter the slot 450 of the retainer collar 422. The length of the cylinder 222 of the power supply mechanism 104 is selected so that the second end or head 164 of the plunger 160 does not touch the first facing surface 230 of the piston 220 when the plunger 160 is fully extended for the maximum volume of liquid medication in the cavity 116 of the syringe 100 and the gripping projection 400 is seated against the front surface 440. (See the cross-sectional view in FIG. 5.)

With the keying tab 402 positioned in alignment with the annular raceway 448, the cartridge cover 420 and the retainer collar 422 can be pivoted from the position shown in FIG. 1, to the position shown in FIG. 2. The annular raceway 448 provides sufficient clearance from the keying tab 402 so that the retainer collar 422 can be pivoted. In the position shown in FIG. 2, the slot 450 of the retainer collar 422 has been pivoted so that it is approximately 90 degrees (one-quarter turn) out of alignment with the keying tab 402. The keying tab 402 is thus constrained by the side of the annular raceway 448 and cannot be moved forward to release the syringe 100 from the power supply mechanism 104. Thus, the keying tab 402 and the annular raceway 448 act together to lock the syringe 100 in the power supply mechanism when the pivotal cover 252 is in the closed position shown in FIG. 2. Therefore, the pressure of the released compressed gas cannot force the syringe 100 out of the power supply mechanism 104. This is believed to be a significant safety feature when the significant pressures generated by the compressed gas are considered.

As shown in FIGS. 1, 2 and 4, the muzzle piece 200 has a slot 460 extending longitudinally through the outside surface of the muzzle piece 200. The slot 460 has a width slightly larger than the width W of the keying tab 402 so that the keying tab 402 can move longitudinally through the slot 460. The slot 460 of the muzzle piece 200 is aligned with the slot 450 of the retainer collar 422 when the pivotal cover 252 is in the loading position shown in FIG. 1 to provide a path by which keying tab 402 of the syringe 100 can be inserted into the retainer collar 422.

Figures 7A, 7B, 7C:
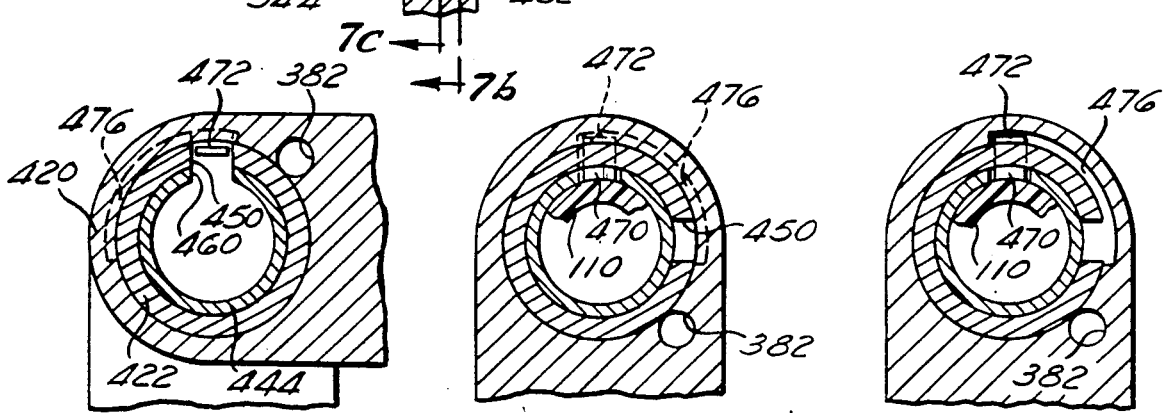
FIG. 7a is a partial cross-sectional view taken along the lines 7a—7a in FIG. 6a to show the interaction of the end of the leaf spring with the sides of the slot in the retainer collar to block the pivoting of the retainer collar.
FIG. 7b is a partial cross-sectional view taken along the lines 7b—7b in FIG. 6b showing the interaction of the wedge-shaped tab of the syringe with the end of the leaf spring to push the end of the leaf spring into the arcuate cavity to allow the retainer collar to be pivoted.
FIG. 7c is a partial cross-sectional view taken along the lines 7c—7c in FIG. 6b which more clearly shows the end of the leaf spring in the arcuate cavity.

As set forth above, the present invention is constructed so that the pivotal cover 252 cannot be closed over the compressed gas cartridge 102 unless the syringe 100 is fully inserted into the power supply mechanism 104. This is accomplished in the preferred embodiment of the present invention by the interaction of a third wedge-shaped projection or tab 470 on the central body portion 110 of the syringe 100 with a leaf spring 472 or other resilient member on the cylinder 222 as shown in FIGS. 5, 6a, 6b, 7a–c, 8 and 9. The leaf spring 472 has a width Ws which is slightly smaller than the width of the slot 450 in the retainer collar 422. The leaf spring 472 has a thickness Ts which is substantially less than the width Ws so that the leaf spring 472 has a preferred direction of flexibility in the direction of the thickness Ts. The leaf spring 472 is preferably constructed of a resilient metal or plastic so that it can be deformed a large number of times in the direction of its thickness and continue to return to its original shape. The leaf spring 472 is mounted on the top of the cylinder 422. A slot 474 is provided on the inner surface of the upper circular opening 266 in the front barrel clamp 260. (See FIGS. 4 and 9 in particular.) The leaf spring 472 is positioned on the top of the cylinder 222 so that a portion of the leaf spring 472 extends beyond the front barrel clamp 260 and into the slot 450 of the rear portion 432 of the retainer collar 422. This is shown in the cross-sectional side view in FIG. 6a and in the cross-sectional end view in FIG. 7a. The position of the leaf spring 472 within the slot 450 causes the sides of the slot 450 to strike the sides of the leaf spring 472 when an attempt is made to pivot the retainer collar 422 when the leaf spring 472 is in the flat undeformed position shown in FIGS. 6a and 7a. Thus, the retainer collar 422 and the cartridge cover 420 of the pivotal cover 252 cannot be pivoted from the open loading position to the closed holding and firing position unless the leaf spring 472 is moved from this blocking position. As shown in FIGS. 6b, 7b, and 7c, the leaf spring 472 is moved from the blocking position to a nonblocking position by the action of the wedge-shaped key 470 on the central body portion 110 of the syringe 100. The wedge-shaped key 470 pushes the leaf spring 472 upward into an arcuate cavity 476 formed in the bore 434 of the cartridge cover 420. The arcuate cavity 476 has depth sufficient to receive the thickness Ts of the leaf spring 472 and has an arcuate length of approximately 90 degrees or one-quarter turn in the direction opposite the direction in which the pivotal cover 252 is moved to the closed or loading position. Thus, the end of the leaf spring 472 is pushed into a position where it no longer interferes with the sides of the slot 450 in the retainer collar 422. The end of the leaf spring 472 moves freely within the arcuate cavity 476 as the pivotal cover 252 is pivoted to the closed holding and firing position. When the pivotal cover 252 is pivoted back to the open loading position and the syringe 100 is removed, the elasticity or resilience of the leaf spring 472 causes the leaf spring 472 to move from the arcuate cavity 476 into an interfering position between the sides of the slot 450 of the retainer collar 422. Since the interaction of the leaf spring 472 with the sides of the slot 450 effectively prevent the pivotal cover 252 from being closed unless a syringe 100 is properly inserted in the power supply mechanism 104, and since the power supply mechanism 104 cannot be triggered unless the pivotal cover 252 is fully closed and the second end 380 of the safety shaft 340 is engaged in the hole 382 of the pivotal cover 252, the power supply mechanism 104 cannot be triggered to release the energy stored in the compressed gas cartridge 102 without a properly installed syringe 100 in the power supply mechanism 104. Thus, the power supply mechanism 104 cannot be used as a power source for a pencil or other potential projectile which may be inserted into the bore 202 of the muzzle piece 200. This is an important feature when the power supply mechanism 104 is accessible by juveniles or juvenile-minded persons who may want to experiment with the power supply mechanism 104.

As shown in cross-section in FIGS. 5–7c, the wedge-shaped key 470 provides additional protection from forward movement of the syringe 100 when the pivotal cover 252 is closed, thus pivoting the slot 450 of the retainer collar 422 out of alignment with the wedge-shaped key 470. In the closed position, the wedge-shaped key 470 cannot be moved forward against the solid portions of the rear portion 432 of the retainer collar 422.

The wedge-shaped key 470, the leaf spring 472 and the arcuate cavity 476 may also be advantageously used to key the syringes 100 and the power supply mechanisms 104 for use with certain specified medications or for certain specified ejection pressures. For example, the depth of the arcuate cavity 476 with respect to the sides of the slot 450 of the retainer collar 422 can be selected so that the end of leaf spring 472 is aligned with the arcuate cavity 476 only when a wedge-shaped key 470 of proper height is used to push the leaf spring 472 into the arcuate cavity 476. If the wedge-shaped key 470 is too short, the end of the leaf spring 472 will continue to interfere with the sides of the slot 450 in the retainer collar 422. If the wedge-shaped key 470 is too tall, the wedge-shaped key 470 will not be able to enter the slot 450 in the retainer collar 422. Thus, the syringes 100 can be advantageously keyed to operate only with power supply mechanisms 104 having dimensions corresponding to the dimensions of the wedge-shaped keys 470 of the syringes 100.

In summary, there are the keying tab 402 and the wedge-shaped key 470 on the central body portion 110 of the syringe 100. The retainer collar 422 forms a pivotal keyway comprising the slot 450 on the end of the power supply mechanism 104. The keyway or slot 450 is pivotal to a first loading position for receiving the keying tab 402 and the wedge-shaped key 470 on the syringe 100 so that the syringe 100 can be inserted into and removed from the power supply mechanism 104. The keyway or slot 450 is pivotal to a second holding position for holding the syringe 100 so that the syringe 100 is irremovably held in the power supply mechanism. The hole 382 in the pivotal cover 252 and the safety shaft 340 operate together to provide a means for selectively blocking movement of the trigger handle 320. When the pivotal cover 252 is open, the safety shaft 340 must be in a first blocking position such that the first end 352 of the safety shaft 340 interferes with the second ear 334 of the trigger handle 320, thus blocking movement of trigger handle 320. When the pivotal cover 252 is closed, the safety shaft 340 can be moved to a second nonblocking position which moves the first end 352 of the safety shaft 340 to a noninterfering position with respect to the second ear 334, thus allowing movement of the trigger handle 320 to the triggering position to release the compressed gas in the gas cartridge 102. The safety shaft 340 is thus mechanically interconnected with the pivotal cover 252 which carries the pivotal keyway or slot 350 so that the safety shaft 340 must be in the second blocking position in order to move the pivotal keyway 350 from the holding position shown in FIG. 2 to the loading position shown in FIG. 1, and so that the pivotal cover 252 must be in the holding position in order to move the safety shaft 340 from the blocking position to the nonblocking position.

As set forth above, the leaf spring 472 and the wedge-shaped tab 470 of syringe 100 provide a means for preventing the pivotal cover 252 carrying the pivotal keyway or slot 450 from moving from the loading position shown in FIG. 1 to the holding position shown in FIG. 2 until the syringe 100 is fully inserted into the power supply mechanism 104 so that the leaf spring 472 is disengaged from the sides of the slot 450 in the retainer collar 422.

The syringe 100 of the present invention further includes means in the form of the heat shrinkable tubing or collar 152 for preventing the syringe 100 from being fully inserted into the power supply mechanism 104 until the needle assembly 120 carrying the needle 122 is removed from the syringe 100.

The operation of the present invention in an exemplary application for injecting a person with insulin or other medication is illustrated in FIGS. 11a–c, 12 and 13. In FIG. 11a, the syringe 100 has the needle assembly 120 still attached. One skilled in the art will appreciate the fact that the syringe 100 is shipped and sold with the needle assembly 120 and thus the needle 122 protected by a cap (not shown) or other means to maintain the needle 122 in a sterile condition and to prevent accidental puncture wounds to the user. The needle 122 is inserted into the protective end seal of a vial 500 of insulin or other medication and the insulin is drawn into the syringe 100 by pulling on the second end 164 of the plunger 160 as shown in FIGS. 11*a* and 11*b*. After the insulin is filled to the appropriate level as indicated by the graduations on the side of the syringe 100 and any air in the syringe removed by pushing on the plunger 160, the needle assembly 120 is removed from the first end 114 of the central body portion of the syringe 100 by pulling on the tab 180 of the heat shrinkable tubing 152 to separate the heat shrinkable tubing 152 at the perforated lines 182*a* and 182*b* (see FIG. 1). Thus, up to the point of removing the needle assembly 120 from the central body portion 110 of the syringe 100, the user of the present invention uses precisely the same procedures that he or she would use with a conventional skin penetrating syringe with a permanently attached needle. In order to further enable a prior use of a skin-penetrating syringe assembly to adapt to the present invention, in the preferred embodiments of the present invention the cavity 116 of the central body portion 110 of the syringe 100 has substantially the same circular cross-section so that a given longitudinal movement of the plunger 160 in the present invention will draw substantially the same volume of liquid medication into the cavity 116 as would be drawn into a conventional syringe by the same amount of movement. Thus, an insulin-dependent diabetic or other long-term medication user who has become accustomed to filling and injecting his or her medication almost instinctively with a consistent movement of the plunger will be able to use the same learned movement with the present invention. The central body portion 110 has graduated markings in accordance with FDA regulations to show the precise amount of medication in the cavity 116 of the syringe 100. The graduations are preferably consistent with the graduations on a corresponding skin-penetrating syringe so that the user can fill the syringe with approximately the same amount of plunger movement as used in a conventional syringe.

After the cavity 116 of the syringe 110 has been filled with the selected volume of medication and the needle assembly 120 removed as described above, the syringe 100 is inserted into the bore 202 of the muzzle piece 200 by inserting the second end 164 of the plunger 160 into the bore 202 first and then sliding the rest of the plunger 160 and the central body portion 110 in afterward, as illustrated in FIG. 12. The gripping projection 400 of the central body portion 110 is positioned so that the user can easily grip the central body portion 110 without positioning his or her fingers near the sterile second end 114 of the central body portion 110. The gripping projection 400 of the central body portion 110 is seated against the front surface 440 of the retainer collar 422. The compressed gas cartridge 102 is inserted into the lower barrel 250 with the first end 296 against the O-ring 294 of the firing pin block 290. (See FIG. 5). The pivotal cover 252 is pivoted to secure the compressed gas cartridge 102 within the lower barrel 250 and to lock the syringe 100 in place. Thereafter, the camming lever 300 is pressed into the closed position to force the second end 296 of the compressed gas cartridge 102 against the O-ring 294 to provide a gas-tight seal as described above.

After the syringe 100 and the compressed gas cartridge 102 are properly loaded, the second end 114 of the syringe 100 is placed against the properly prepared skin 510 of the user as illustrated in FIG. 13. The safety shaft 340 (not shown) is moved from its blocking to its nonblocking position by moving the finger grip 346 forward. Pressure is applied to the trigger handle 320 to force the trigger handle 320 towards the lower barrel 250. As described above, this action causes the camming surface 328 (see FIGS. 3 and 5) of the trigger handle 320 to force the firing pin 310 (shown in phantom) through the sealed first end 296 of compressed gas cartridge 102 (shown in phantom). The compressed gas (or liquified gas) within the compressed gas cartridge 102 is released and conducted via the tube 366 (shown in phantom) and the gas conducting path 376 (shown in phantom) in the rear breechblock 262 to the piston 220 (shown in phantom). The piston 220 is forced to move forward wherein it engages the second end 164 of the plunger 160 (both shown in phantom) and thus forces the plunger 160 forward against the liquid medication contained within the syringe 100. The liquid medication is forced through the aperture 118 (not shown) of the second end 114 of the central body portion 110 of the syringe 100, and, if the second end 114 is held securely against the skin 510 of the user, the liquid medication is ejected through the aperture 118 with sufficient force to penetrate the skin 510 and enter the tissues beneath the skin 510. The operation of the present invention leaves no puncture wound and causes very little pain to the user.

After the liquid medication has been injected into the person's tissues as described above, the safety shaft 340 is moved to the blocking position and the pivotal cover is opened to remove the exhausted compressed gas cartridge 102 and the empty syringe 100. Both the syringe 100 and the compressed gas cartridge 102 are discarded. Each syringe 100 comes with a sterilized second end 114 which is the only part of the present invention to contact the person's skin in the area of the injection site. Since no part of the power supply mechanism 104 which remains has contacted the person's skin in the area where the injection occurs and will not contact the area of future injections, there is no need to sterilize the power supply mechanism 104. Thus, routine cleaning of the power supply mechanism 104 is adequate to maintain the power supply mechanism 104 in usable condition.

The apparatus of the present invention is particularly suited for personal use because of its size and shape. Many of the prior art devices using compressed gas or a spring for a power source have the power source aligned with the ampule containing the liquid medication. Thus, many of the prior art devices are quite long and present problems in carrying them and using them. Other prior art devices require elaborate assembly procedures for inserting and securing the medication ampules and the compressed gas source. As set forth above, both of these set of problems are solved in the present invention by positioning the lower barrel 250 and the upper cylinder 222 in juxtaposed relationship so that the compressed gas container 102 and the syringe 100 can be inserted into the power supply mechanism 104 from the same direction and secured therein at the same time by closing the pivotal cover 252.

Since the lower barrel 250 and the cylinder are side-by-side, the total length of the device is substantially reduced as compared to prior art devices which typically had the medication ampule and the compressed gas source aligned along the same axis. The present invention allows the side-by-side alignment of the syringe 100 and the compressed gas container 102 by providing the U-shaped gas conductor path 376 through the rear breechblock 262.

While preferred embodiments of this invention have been disclosed herein, those skilled in the art will appreciate that changes and modifications may be made therein without departing from the spirit and scope of this invention as defined in the appended claims.

What is claimed is:

1. An apparatus for injecting liquid medication through the skin of a person without puncturing the skin, while providing for filling of the medication in the conventional manner used to fill syringes for subcutaneous injections comprising:
   a disposable syringe comprising:
      a cavity for holding a liquid medication;
      an aperture in a first end of said syringe through which said liquid medication can flow into and out of said cavity; and
      a plunger moveable within said cavity for drawing said liquid medication into said cavity and for forcing said liquid medication out of said cavity;
   a needle removably attached to said first end of said syringe in substantial alignment with said aperture, said needle insertable into a container of said liquid medication so that a selectively variable volume of liquid medication can be drawn into said cavity through said needle and said aperture, the amount of said liquid being that which is needed by the individual, said needle being removable from said syringe after drawing said liquid medication into said cavity so that said first end of said syringe can be placed in contact with the skin without puncturing the skin; and
   a power supply mechanism for receiving and securely holding said syringe and for providing pressure to forcefully move said plunger in said cavity against said liquid medication so that said liquid medication is ejected through said aperture, said power supply mechanism comprising:
      a cylinder;
      a piston within said cylinder, said piston moveable against said plunger of said syringe to force said liquid medication out of said cavity of said syringe;
      a chamber for receiving a sealed container of a compressed gas;
      trigger means for unsealing the sealed container to release said compressed gas when force is applied to said trigger means;
      means for conducting said released compressed gas to said piston, so that said piston is moved against said plunger to move said plunger against said liquid medication to eject said liquid medication from said cavity through said aperture, said piston and said plunger operable to multiply the pressure provided by said compressed gas to a pressure against said liquid medication sufficient to force said liquid medication through the skin;
      first safety means for preventing said syringe from being fully inserted into said power supply mechanism while said needle is attached to said syringe so that the power supply mechanism cannot be used to force out the liquid medication; and
      second safety means for preventing said power supply mechanism from releasing said compressed gas until said syringe is fully inserted so that said power supply mechanism cannot be used to eject objects from said power supply mechanism.

2. An apparatus for injecting liquid medication through the skin of a person without puncturing the skin, comprising:
   a disposable syringe comprising:
      a cavity for holding a liquid medication;
      an aperture in a first end of said syringe through which said liquid medication can flow into and out of said cavity; and
      a plunger moveable within said cavity for drawing said liquid medication into said cavity and for forcing said liquid medication out of said cavity;
   a needle removably attached to said first end of said syringe in substantial alignment with said aperture, said needle insertable into a container of said liquid medication so that said liquid medication can be drawn into said cavity through said needle and said aperture, said needle being removable from said syringe after drawing said liquid medication into said cavity so that said first end of said syringe can be placed in contact with the skin without puncturing the skin; and
   a power supply mechanism for receiving and securely holding said syringe only after said needle is removed from said syringe and for providing pressure to forcefully move said plunger in said cavity against said liquid medication so that said liquid medication is ejected through said aperture with sufficient pressure that the liquid medication will penetrate the skin of a person when said first end of said syringe is placed in substantial contact with the skin.

3. The apparatus as defined in claim 2, wherein said power supply mechanism comprises:
   a cylinder;
   a moveable piston within said cylinder, said piston having an axis of movement within said cylinder substantially aligned with said plunger in said syringe when said syringe is in said power supply mechanism, said piston moveable against said plunger to force said liquid medication out of said cavity in said syringe;
   a chamber for receiving a sealed container of a compressed gas;
   means for unsealing the sealed container to release said compressed gas;
   a trigger means mechanically attached to said means for unsealing so that said sealed container is unsealed when force is applied to said trigger;
   means for conducting said compressed gas to said piston, said compressed gas thereby applying a force to said piston so that said piston is moved against said plunger to move said plunger against said liquid medication to eject said liquid medication from said cavity through said aperture with a pressure sufficient to force the liquid medication through the skin; and
   safety interlocking means for preventing movement of said trigger means to thereby prevent said unsealing means from unsealing said sealed container of compressed gas except when said syringe is secured within said power supply mechanism.

4. The apparatus as defined in claim 3, further including a key on said syringe, and wherein said safety interlocking means on said supply mechanism comprises:
   a pivotal keyway on the end of said power supply mechanism, said keyway being pivotal to a first loading position for receiving said key on said syringe so that said syringe can be inserted into and removed from said power supply mechanism, said keyway being pivotal to a second holding position for holding said syringe so that said syringe is irremovably held in said power supply mechanism; and means for selectively blocking movement of said trigger means, said means for selectively blocking having a first blocking position for blocking movement of said trigger means and having a second nonblocking position for allowing movement of said trigger means, said means for selectively blocking movement mechanically interconnected with said pivotal keyway so that said means for selectively blocking movement must be in said second blocking position in order to move said pivotal keyway from said holding position to said loading position and so that said pivotal keyway must be in said holding position in order to move said means for selectively blocking from said blocking position to said nonblocking position.

5. The apparatus as defined in claim 4 further including means for preventing said pivotal keyway from moving from said loading position to said holding position until said syringe is fully inserted into said power supply mechanism.

6. The apparatus as defined in claim 5 wherein said syringe includes means for preventing said syringe from being fully inserted into said power supply mechanism until said needle is removed from said syringe.

7. The apparatus as defined in claim 6 wherein said means for preventing said syringe from being fully inserted into said power supply mechanism until said needle is removed from said syringe is a collar holding said needle to said syringe, said collar having an outer dimension too large to fit within said power supply mechanism.

8. An apparatus for injecting liquid medication through the skin of a person without puncturing the skin, comprising:

a disposable syringe having a removable needle for filling said syringe with said liquid medication; and a power supply mechanism for receiving and securing said syringe only after said needle is removed and for forcing said liquid medication from said syringe with sufficient force to penetrate said skin when said syringe is in substantial contact with said skin.

9. The apparatus as defined in claim 8 wherein said power supply mechanism includes a locking means and said syringe includes a keying means, and wherein said power supply mechanism is operable to force said liquid medication from said syringe only when said keying means engages with and releases said locking means.

10. A method of injecting a liquid medication through the skin without puncturing the skin comprising the steps of:

filling a syringe having a removable needle on one end with said liquid medication through said needle;

removing said needle from said one end of said syringe;

inserting said syringe in a power supply mechanism;

inserting a container of compressed gas into said power supply mechanism;

securing said syringe and said container in said power supply mechanism;

positioning said one end of said syringe against said skin; and activating said power supply mechanism to forcefully eject said liquid medication through said skin.

11. An apparatus for injecting liquid medication through the skin of a person, comprising:

a syringe;

removable means for filling said syringe with said liquid medication;

means for applying sufficient pressure to said liquid medication within said syringe to force said liquid medication out of said syringe through the skin; and means for preventing said pressure from being applied to said liquid medication in said syringe while said removable means is attached to said syringe.

12. The apparatus as defined in claim 11 wherein said means for applying pressure is a power supply mechanism having a removable container of compressed gas, said gas releasable from said container to apply said pressure to said medication.

13. The apparatus as defined in claim 12 wherein said power supply mechanism includes means for preventing the release of said gas from said container unless said syringe is secured in said power supply mechanism.

14. A syringe for injection of a liquid medication through the skin without puncturing the skin, said syringe being adapted to operate with a source of high pressure, said syringe comprising:

a removable means for filling said syringe from a container of said liquid medication;

a plunger for ejecting said liquid medication from said syringe, said plunger positionable to receive pressure from said source of high pressure; and means on said syringe for preventing said syringe from being inserted into said source of high pressure with said removable means attached to said syringe.

15. The syringe as defined in claim 14 further including means for keying said syringe to said source of high pressure so that said syringe is insertable into said source of high pressure.

16. An apparatus for injecting liquid medication through the skin of a person without puncturing the skin, comprising:

a disposable syringe comprising:

a tubular central body portion having a open first end and a substantially closed second end to form an enclosed cavity within said central body portion, said second end having an aperture formed therein to provide means for fluid communication through said second end into said cavity;

a hollow tubular needle removably attached to said second end of said central body portion in substantial alignment with said aperture, said needle insertable into a container of said liquid medication; and a plunger having a first end within said cavity of said central body portion and a second end extending out of said cavity in a direction opposite said second end of said central body portion, said plunger being movable within said cavity in a first direction away from said second end to create a vacuum within said cavity to draw said liquid medication through said needle and said aperture into said cavity, said plunger being moveable in a second direction towards said second end of said central body portion to force said liquid medication from said cavity through said aperture in said second end;

said needle being removable from said second end of said central body portion after drawing said liquid medication into cavity of said said central body portion so that said second end of said central body portion can be placed in contact with the skin without puncturing the skin; and a power supply mechanism for receiving and securely holding said syringe only after said needle is removed from said second end of said central body portion and for providing pressure to move said plunger in said second direction towards said second end of said central body portion so that said liquid medication in said cavity of said syringe is ejected through said aperture of said second end with sufficient pressure that the liquid medication will penetrate the skin of a person when said second end is placed in substantial contact with the skin, said power supply mechanism comprising:

a resiliently biased moveable piston within a cylinder, said piston having an axis of movement within said cylinder substantially aligned with the first and second directions of movement of said plunger, said piston having a first facing surface directed towards said plunger of said syringe and a second facing surface directed away from said plunger of said syringe, said piston biased to a position in said cylinder away from said plunger of said syringe in said mechanism;

a removable sealed container of a compressed gas;

means for unsealing the sealed container to release said compressed gas, said means for unsealing positiioned for mechanical interaction with a moveable trigger means so that said sealed container is unsealed when force is applied to said trigger means;

means for conducting said compressed gas to said second surface of said piston, said compressed gas thereby applying a force on said second surface of said piston so that said piston is moved in said second direction against said resilient biasing and forces said plunger to move in said second direction to eject said liquid modification from said cavity through said aperture with a pressure sufficient to force the liquid medication through the skin; and safety interlocking means for preventing movement of said trigger means to thereby prevent said unsealing means from unsealing said sealed container of compressed gas except when said syringe is secured within said power supply mechanism.

17. The apparatus as defined in claim 16, wherein said safety interlocking means comprises:

a key on said syringe;

a pivotal keyway on the end of said power supply mechanism, said keyway being pivotal to a first loading position for receiving said key on said syringe so that said syringe can be inserted into and removed from said power supply mechanism, said keyway being pivotal to a second holding position for holding said syringe so that said syringe is irremovably held in said power supply mechanism; and means for selectively blocking movement of said trigger means, said means for selectively blocking having a first blocking position for blocking movement of said trigger means and having a second nonblocking position for allowing movement of said trigger means, said means for selectively blocking movement mechanically interconnected with said pivotal keyway so that said means for selectively blocking movement must be in said second blocking position in order to move said pivotal keyway from said holding position to said loading position and so that said pivotal keyway must be in said holding position in order to move said means for selectively blocking movement from said blocking position to said nonblocking position.

18. The apparatus as defined in claim 17 further including means for preventing said pivotal keyway from moving from said loading position to said holding position until said syringe is fully inserted into said power supply mechanism.

19. The apparatus as defined in claim 18 wherein said syringe includes means for preventing said syringe from being fully inserted into said power supply mechanism until said needle is removed from said syringe.

20. An improved syringe for use in a system for injecting liquid medication through the skin of a person without puncturing the skin, in which said syringe is insertable into a power supply mechanism having a container of compressed gas and said power supply mechanism includes means for selectively releasing said compressed gas to force the liquid medication out of said syringe at a high pressure, wherein the improvement comprises:

filling means removably attached to one end of said syringe, said filling means insertable into a vial of said liquid medication;

a plunger positioned within said syringe, said plunger operable in a first direction to create a vacuum within said syringe to draw said liquid medication through said filling means into said syringe and operable in a second direction to force said liquid medication from said syringe through said one end; and means for preventing said syringe from being inserted into said power supply mechanism with said filling means attached to said syringe.

21. The improvement in said syringe as defined in claim 20 wherein said means for preventing said syringe from being inserted into said power supply mechanism with said filling means attached comprises a collar binding said filling means to said syringe, said collar being too large to fit within said power supply mechanism.

22. The improvement in said syringe as defined in claim 20 wherein said syringe further comprises at least one key on a surface of said syringe, said key being operable within said power supply mechanism to unlock a safety interlocking means within said power supply mechanism which prevents the operation of said means for selectively releasing said compressed gas until said syringe is fully inserted in said power supply mechanism.

23. The improvement in said syringe as defined in claim 20 wherein said syringe further comprises a gripping surface disposed away from said one end so that said syringe can be inserted into said power supply mechanism without touching said one end of said syringe.

24. An apparatus for injecting liquid medication through the skin of a person without puncturing the skin, comprising:
   a removable syringe for holding said liquid medication;
   a container of compressed gas; and
   a power supply mechanism for receiving said removable syringe and said container and securing said syringe and said container in parallel relationship, said power supply mechanism further including trigger means for releasing said compressed gas from said container and means for conducting said compressed gas from said container to said syringe to force said liquid medication from said syringe with sufficient pressure to force said liquid medication from said syringe and through the skin when said syringe is positioned against the skin, said power supply mechanism further including a means for allowing said trigger means to release said compressed gas only when said removable syringe is secured within said power supply mechanism.

25. An apparatus for injecting a liquid medication through the skin of a person without puncturing the skin, comprising:
   a syringe for receiving a selectable volume of said liquid medication, said syringe having a plunger for drawing said medication into said syringe;
   a sealed container of compressed gas;
   a power supply mechanism for receiving said syringe and said container and holding said syringe and said container in juxtaposed parallel relationship, said power supply mechanism comprising:
   a barrel for holding said container;
   a firing pin positioned in alignment with said container;
   a trigger handle for forcing said firing pin against said container to unseal said container and release said compressed gas;
   a cylinder for holding said syringe, said cylinder juxtaposed in parallel relationship with said barrel;
   a piston within said cylinder aligned with said plunger of said syringe;
   a U-shaped conduction path for conducting said released gas from said container to said cylinder to thereby force said piston within said cylinder against said plunger to force the liquid medication out of said syringe; and
   safety means to block movement of said trigger means to prevent said firing pin from unsealing said container unless said syringe is securely held within said power supply mechanism.

* * * * *

UNITED STATES PATENT AND TRADEMARK OFFICE
CERTIFICATE OF CORRECTION

PATENT NO. : 4,680,027

DATED : July 14, 1987

INVENTOR(S) : James S. Parsons and Jack S. Gasaway

It is certified that error appears in the above-identified patent and that said Letters Patent is hereby corrected as shown below:

Column 9, line 33, change "surface" to --lever--.

Signed and Sealed this

Sixth Day of December, 1988

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO. : 4,680,027
DATED : July 14, 1987
INVENTOR(S) : James S. Parsons and Jack S. Gasaway It is certified that error appears in the above-identified patent and that said Letters Patent is hereby corrected as shown below:

Column 9, line 11, change "surface" to --lever--

This certificate supersedes Certificate of Correction issued December 6, 1988.

Signed and Sealed this

Seventh Day of November, 1989

*Attest:*

JEFFREY M. SAMUELS

*Attesting Officer*     *Acting Commissioner of Patents and Trademarks*